US006080751A

United States Patent [19]
Stehlin et al.

[11] Patent Number: 6,080,751
[45] Date of Patent: *Jun. 27, 2000

[54] METHOD FOR TREATING PANCREATIC CANCER IN HUMANS WITH WATER-INSOLUBLE S-CAMPTOTHECIN OF THE CLOSED LACTONE RING FORM AND DERIVATIVES THEREOF

[75] Inventors: John S. Stehlin; Ethan A. Natelson; Beppino C. Giovanella; Anthony J. Kozielski, all of Houston, Tex.

[73] Assignee: The Stehlin Foundation for Cancer Research, Houston, Tex.

[ * ] Notice: This patent is subject to a terminal disclaimer.

[21] Appl. No.: 08/713,392

[22] Filed: Sep. 13, 1996

Related U.S. Application Data

[63] Continuation-in-part of application No. 08/474,761, Jun. 7, 1995, Pat. No. 5,652,244, which is a continuation of application No. 08/002,844, Jan. 15, 1993, abandoned, which is a continuation-in-part of application No. 07/820,334, Jan. 14, 1992, abandoned, and a continuation-in-part of application No. 07/432,066, Nov. 6, 1989, Pat. No. 5,225,404.

[51] Int. Cl.[7] .................................................. A61K 31/44
[52] U.S. Cl. ......................................................... 514/283
[58] Field of Search ............................................. 514/283

[56] References Cited

U.S. PATENT DOCUMENTS

| | | | |
|---|---|---|---|
| Re. 32,518 | 10/1987 | Miyasaka et al. ......................... | 546/48 |
| 3,894,029 | 7/1975 | Winterfeldt et al. .................... | 424/258 |
| 4,031,098 | 6/1977 | Sugasawa ................................. | 424/258 |
| 4,357,422 | 11/1982 | Giard et al. .............................. | 435/68 |
| 4,399,276 | 8/1983 | Miyasaka et al. ......................... | 546/48 |
| 4,399,282 | 8/1983 | Miyasaka et al. ......................... | 546/48 |
| 4,473,692 | 9/1984 | Miyasaka et al. ......................... | 546/48 |
| 4,513,138 | 4/1985 | Miyasaka et al. ......................... | 546/48 |
| 4,545,880 | 10/1985 | Miyasaka et al. ....................... | 204/158 |
| 4,604,463 | 8/1986 | Miyasaka et al. ......................... | 546/48 |
| 4,774,236 | 9/1988 | Cook et al. ............................... | 546/48 |
| 4,867,978 | 9/1989 | Gold ......................................... | 424/166 |
| 4,874,779 | 10/1989 | Senter ...................................... | 514/410 |
| 4,894,456 | 1/1990 | Wall et al. ................................ | 546/48 |
| 4,904,768 | 2/1990 | Saulnier et al. ......................... | 536/17.1 |
| 4,914,205 | 4/1990 | Sawada et al. ............................ | 546/48 |
| 4,939,255 | 7/1990 | Tagawa et al. ............................ | 546/48 |
| 4,943,579 | 7/1990 | Vishnuvajjala et al. ................. | 514/283 |
| 4,981,968 | 1/1991 | Wall et al. ................................ | 546/48 |
| 5,004,758 | 4/1991 | Boehm et al. ............................ | 514/283 |
| 5,041,424 | 8/1991 | Saulnier et al. ......................... | 514/27 |
| 5,049,668 | 9/1991 | Wall et al. ................................ | 546/48 |
| 5,053,512 | 10/1991 | Wani et al. .............................. | 546/48 |
| 5,061,795 | 10/1991 | Tagawa et al. ............................ | 546/48 |
| 5,061,800 | 10/1991 | Yaegashi et al. ......................... | 546/48 |
| 5,064,823 | 11/1991 | Lee et al. ................................. | 514/98 |
| 5,106,742 | 4/1992 | Wall et al. ................................ | 514/283 |
| 5,122,526 | 6/1992 | Wall et al. ................................ | 546/48 |
| 5,122,606 | 6/1992 | Wani et al. .............................. | 546/48 |
| 5,126,351 | 6/1992 | Luzzio et al. ............................ | 514/291 |
| 5,145,684 | 9/1992 | Liversidge et al. ...................... | 424/489 |
| 5,155,225 | 10/1992 | Fortunak et al. ......................... | 546/48 |
| 5,162,532 | 11/1992 | Comins et al. .......................... | 546/48 |
| 5,180,722 | 1/1993 | Wall et al. ................................ | 514/219 |
| 5,225,404 | 7/1993 | Giovanella et al. ..................... | 514/283 |

FOREIGN PATENT DOCUMENTS

| | | |
|---|---|---|
| 0 074 256 | 3/1983 | European Pat. Off. . |
| 0 220 601 | 5/1987 | European Pat. Off. . |
| 0 418 099 A2 | 3/1991 | European Pat. Off. . |
| 0 540 099 A1 | 5/1993 | European Pat. Off. . |
| 61-50985 | 3/1983 | Japan . |
| 59-5188 | 1/1984 | Japan . |
| 59-501288 | 3/1984 | Japan . |
| 59-51289 | 3/1984 | Japan . |
| 61-85319 | 4/1986 | Japan . |
| 61-85389 | 4/1986 | Japan . |
| WO 91/05556 | 5/1991 | WIPO . |
| WO 91/16904 | 11/1991 | WIPO . |

OTHER PUBLICATIONS

1992 AACR Abstract Form, "Pharmacokinetics of Tritum Labeled Camptothecin in Nude Mice," Smith, P.L. et al.

1992 AACR Abstract Form, "Growth Inhibition of Human cancer Metasteses in the Xenograft Model by Camptothecin [NSC 94600], 9–amino (NSC 60371] and 9–nitrocamptothecin," Potmesil, M.

Giovanella et al., Cancer Research, vol. 51, pp. 3052–3055, Jun. 1, 1991.

Kharbanda et al., Cancer Research, vol. 51, pp. 6636–6642, Dec. 15, 1991.

*The Alkaloids,* vol. XXV, Chapter 1, "Antitumor Alklaoids," Suffness et al., pp. 73–89, copyright 1985, Academic Press, Inc.

Wall et al., "New Type of 9–Nitrocamptothecin and a Method of its Production," J. Am. Chem. Soc., vol. 88, No. 16, pp. 3888–3890, Aug. 20, 1966.

Hsiang, Y.–H. et al., Cancer Res. 48: 1722–1726, 1988.

Wani, M.C. et al., J. Med. Chem. 30: 1774–1779, 1987.

Wani, M.C. et al., J. Med. Chem 29: 2358–2363, 1986.

Hsiang, Y.–H. et al., J. Biol. Chem 97: 14873–14878, 1985.

Hsiang, Y.–H. et al., Abstract 683 from The American Association for Cancer Research, vol. 29, Mar. 1988.

Wall, M.E. et al., J. Med. Chem. 29: 1553–1555, 1986.

Nelson, W.G. et al., Cancer Res. 47: 3246–3250, 1987.

Hsiang, Y.–H. et al., Cancer Res. 49: 4386–4389, 1989.

Wani, M.C. et al., J. Med. Chem. 30: 2317–2319, 1987.

Giovanella, B.C. et al., Cancer 52: 1146–1152, 1983.

Wani, M.C. et al., J. Med. Chem. 23: 554–560, 1980.

Leibovitz, A. et al., Cancer Res. 36: 4562–4569, 1976.

Fogh, J. et al., in "Human Tumor Cells In Vitro," Fogh, Jr. et., Plenum Press, New York, 1976, pp. 115–141.

(List continued on next page.)

*Primary Examiner*—Jerome D. Goldberg
*Attorney, Agent, or Firm*—Armstrong, Westerman, Hattori, McLeland & Naughton

[57] ABSTRACT

A method of treating human pancreatic cancer with water-insoluble 20(S)-camptothecin compounds with the closed-lactone ring intact and/or derivatives thereof is disclosed. The method includes preferably administering the compounds intramuscularly, orally, and transdermally.

9 Claims, 1 Drawing Sheet

OTHER PUBLICATIONS

Liu, L.F. et al., Proc. Nat'l. Acad. Sci. USA, 78: 3487–3491, 1981.
Muggla, F.M. et al., Cancer Chemo. Rep. 56: 515–521, 1972.
Gottlieb, J.A. et al., Cancer Chemo. Rep. 54: 461–470, 1970.
Jaxel,C. et al., Cancer Res. 49: 1465–1469, 1989.
Potmesil, M. et al., Cancer Res. 48: 3537–3543, 1988.
Chemical Abstracts, vol. 106(25), Abstract No. 207285z (1987).
Chemical Abstracts, vol. 106(15), Abstract No. 120133z (1987).
Chemical Abstracts,vol. 106(15), Abstract No. 11479a (1987).
Chemical Abstracts,vol. 106(13), Abstract No. 95753s (1987).
Chemical Abstracts, vol. 103(9), Abstract No. 64374c (1985).
Chemical Abstracts, vol. 101, Abstract No. 130677r (1984).
Chemical Abstracts, vol. 101(11), Abstract No. 91322z (1982).
Chemical Abstracts, vol. 101(10), Abstract No. 78770z (1984).
Chemical Abstracts, vol. 100(21), Abstract No. 167724j (1983).
Chemical Abstracts, vol. 100, Abstract No. 139434w (1984).
Chemical Abstracts, vol. 97, Abstract No. 188278b (1982).
Chemical Abstracts, vol. 96(9), Abstract No. 69271p (1981).
Chemical Abstracts, vol. 95(15), Abstract No. 133209h (1981).
Chemical Abstracts, vol. 94(1), Abstract No. 4143n (1980).
Chemical Abstracts, vol. 92(5), Abstract No. 37766e (1980).
Chemical Abstracts, vol. 92(3), Abtract No. 18799b (1980).
Chemical Abstracts, vol. 90(4), Abstract No. 28930k (1979).
Chemical Abstracts, vol. 90(3), Abstract No. 22857v (1979).
Chemical Abstracts, vol. 84, Abstract No. 115629p (1976).
Chemical Abstracts, vol. 94(12), Abstract No. 90169e (1980).
Derwent 89–179979/25.
Nicholas et al., J. Med. Chem., vol. 33, No. 3, pp. 972–978, 1990.
Ohro et al., Proc. Ann. Meet Am. Soc. Clin. Oncol., 8: A1019, 1989.
Hertzberg et al., J. Med. Chem., vol. 32(3), pp. 715–720, 1989.
Hsiang et al., Proc. Ann. Meet. Am. Assoc. Cancer Res., 30: A2476, 1989.
Hertzberg et al., Proc. Ann. Meet. Am. Assoc. Cancer Res., 30: A2485, 1989.
Pommier et al., Proc. Ann. Meet. Am. Assoc. Cancer Res., 29: A1080, 1988.
Lin et al., Yao Hsueh Hsueh Pao, vol. 23(3), pp. 186–188 (1988).
Ronman et al., Journal of Labelled Compounds and Radiopharmaceuticals, vol. 18(3), pp. 319–329, 1981.
Danishefky et al., J. Org. Chem., vol. 39(28), pp. 3430–3432, 1974.
Plattner et al., J. Org. Chem., vol. 39(3), pp. 303–311, 1974.
Plattner et al., J. Amer. Chem. Soc., vol. 94(24), pp. 8615–8616, 1972.
Govindachari et al., "9–Methoxycamptothecin: a New Alkaloid from Mappie voetida Miers,"pp. 453–454.
Giovanella et al., Science, vol. 246, pp. 1046–1048, 1989.
Xi–Ran et al., "Topical Camptothecine in Treatment of Psoriasis," Int'l Journal of Dermatology, vol. 27, No. 7, pp. 475–476, Sep. 1988.
Ching–jung et al., "Effect of Topical Use of Camptothecine–Dimethyl Sulfoxide Solution in Psoriasis," Chinese Medical Journal, vol. 1, No. 5, pp. 355–360, Sep. 1975.
Tung et al., "Camptothecin Instillation and Local Injection for Prevention and Treatment of Urinary Bladder Tumors," Chinese Medical Journal, vol. 92, No. 1, pp. 57–60, 1979.
Pantazis et al., "Complete Inhibition of Growth Followed by Death of Human Malignant Melanoma Cells in Vitro and Regression of Human Melanoma Xenografts in Immunodeficient Mice Induced by Camptothecin," Cancer Research, vol. 52, No. 14, pp. 3980–3987, Jul. 15, 1992.
Cancer Research 5. 3980–3987, Jul. 15, 1992; "Complete Inhibition of Growth followed by Death of Human Malignant Melanoma Cells in Vitro and Regression of Human Melanoma Xenografts in Immunodeficient Mice Induced by Camptothecins[1]."

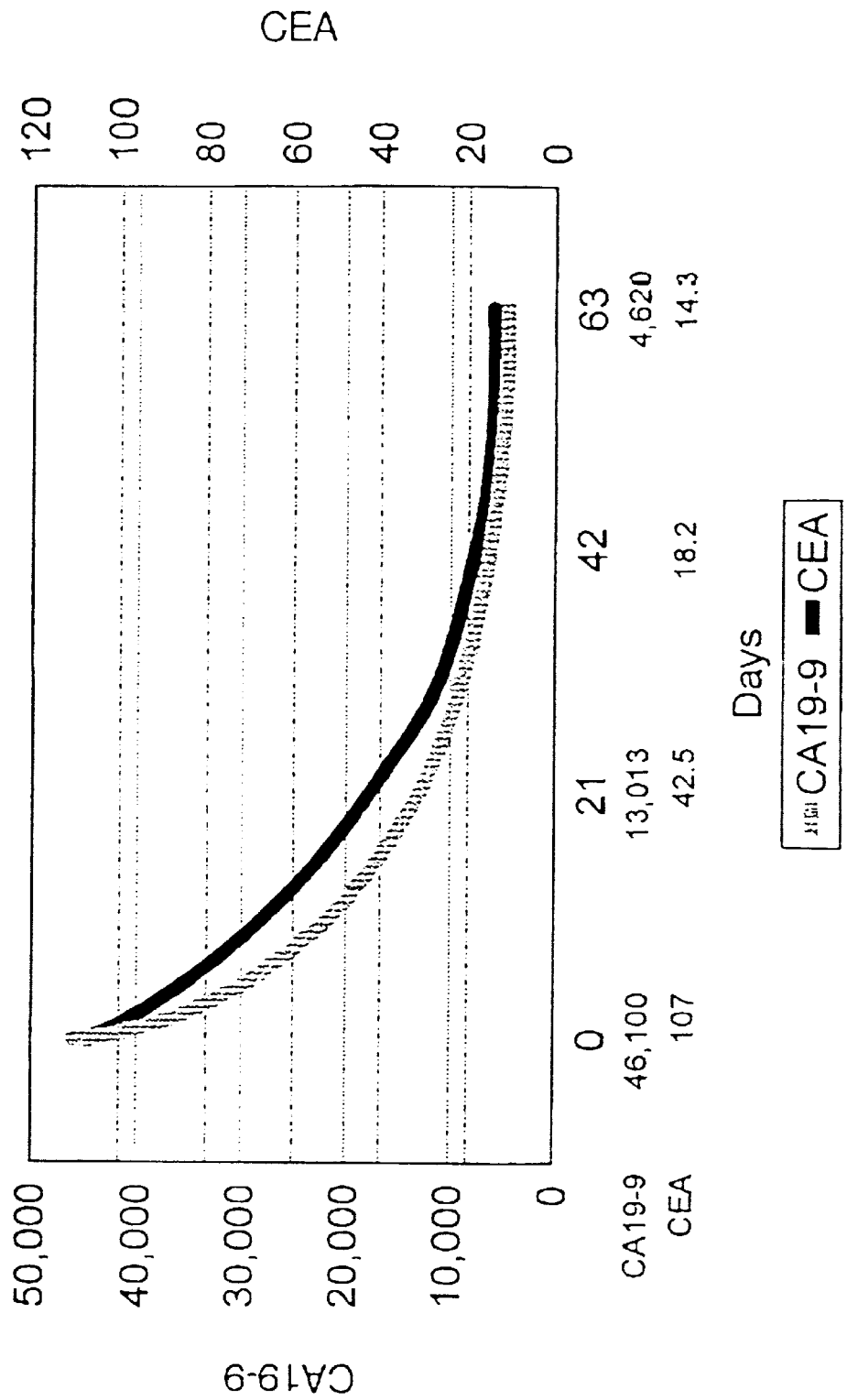

METHOD FOR TREATING PANCREATIC CANCER IN HUMANS WITH WATER-INSOLUBLE S-CAMPTOTHECIN OF THE CLOSED LACTONE RING FORM AND DERIVATIVES THEREOF

This application is a continuation-in-part of U.S. Ser. No. 08/474,761, filed Jun. 7, 1995, now U.S. Pat. No. 5,652,244 which is a continuation of U.S. Ser. No. 08/002,844, filed Jan. 15, 1993, abandoned which is a continuation-in-part of U.S. Ser. No. 07/820,334, filed Jan. 14, 1992, abandoned, and also a continuation-in-part of U.S. Ser. No. 07/432,066, filed Nov. 6, 1989, now U.S. Pat. No. 5,225,404.

FIELD OF THE INVENTION

The present invention relates to a method for treating pancreatic cancer in humans.

BACKGROUND OF THE INVENTION

20(S)-camptothecin (CPT), a plant alkaloid, was found to have anticancer activity in 1966 (Wall, M., Wani, M. C., Cooke, C. E., Palmer, K. H., McPhail, A. T. and Slim, G. A. "Plant antitumor agents. I. The isolation and structure of camptothecin, a novel alkaloidal leukemia and tumor inhibitor from *Camptotheca acuminata*", *J. Am. Chem. Soc.* 88: 3888–3890, 1966).

During the sixties and seventies the sodium salt of CPT was derived from CPT, and clinical trials of this chemically altered CPT were carried out and then abandoned because of the high toxicity and low potency of this compound (Gottlieb, J. A., Guarino, A. M., Call, J. B., Oliverio, V. T. and Block, J. B. "Preliminary pharmacological and clinical evaluation of camptothecin sodium salt (NSC 100880)", *Cancer Chemother. Rep.* 54: 461–470; 1979; Muggia, F. M., Creaven, P. J., Hansen, H. H., Cohen, M. N. and Selawry, D. S. "Phase I clinical trials of weekly and daily treatment with camptothecin (NSC 100880). Correlation with clinical studies." *Cancer Chemother. Rep.* 56: 515–521; 1972; Gottlieb, J. A. and Luce, J. K. "Treatment of malignant melanoma with camptothecin (NSC 100880)." *Cancer Chemother. Rep.* 56: 103–105; 1972; and Moertel, C. G., Schutt, A. J., Reitemeier, R. J. and Hahn, R. G. "Phase II study of camptothecin (NSC 100880) in the treatment of advanced gastrointestinal cancer." *Cancer Chemother. Rep.* 56: 95–101; 1972. All these trials were conducted using the hydrosoluble, sodium salt derivative of CPT (CPT Na+), which was administered via i.v. The research of the present inventors has fully confirmed the ineffectiveness and the toxicity of CPT Na+.

Experiments have demonstrated that the non-water soluble CPT is nontoxic and highly effective as an anticancer agent. Furthermore, the present inventors have demonstrated that the intramuscular and oral administration provide unexpectedly better results than the intravenous administration.

Drug therapies have been evaluated with respect to treating human cancer, e.g., human cancer xenograft lines. Human tumors are serially heterotransplanted into immunodeficient, so-called "nude" mice, and the mice then tested for their responsiveness to a specific drug. (Giovanella, B. C., et al., *Cancer* 52(7):1146 (1983)). The data obtained in these studies strongly support the validity of heterotransplanted human tumors into immunodeficient mammals, such as nude mice, as a predictive model for testing the effectiveness of anticancer agents.

It was determined that 9-Amino-20(S)-Camptothecin (9AC) and 10,11-Methylendioxy-20(S)-Camptothecin (10, 11MD) are capable of having high anticancer activity against human colon cancer xenografts (Giovanella, B. C., Wall, M. E., Wani, M. C., Nicholas, A. W., Liu, L. F., Silber, R. and Potmesil, M. "Highly effective topoisomerase-I targeted chemotherapy of human colon cancer in xenografts." *Science* 246: 1046–1048; 1989). After this finding, the present inventors extended these studies to other human cancers growing as xenografts in nude mice as well as conducted studies on the administration of CPT and its derivatives. It is important to note that the fundamental difference between the chemical used by the present invention (CPT) and the one used ineffectively and with high attendant toxicity in the past (CPT Na+) is that CPT is water-insoluble and CPT Na+ is water-soluble.

SUMMARY OF THE INVENTION

An object of the present invention is to provide a novel method for treating pancreatic cancer in humans.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

To achieve the objects and in accordance with the purpose of the present invention, as embodied and broadly described herein, the present invention relates to a method for treating pancreatic cancer in a human which comprises administering an effective amount of a water-insoluble 20(S)-Camptothecin (CPT) with the closed-lactone ring intact or a derivative thereof or a mixture thereof, preferably 9-nitro-20(S)-camptothecin.

It is to be understood that both the foregoing general description and the following detailed description are exemplary and explanatory only and are not restrictive of the present invention, as claimed.

BRIEF DESCRIPTION OF THE DRAWING

The Figure is a graph showing the results obtained by administering 9-Nitro-20(S)-camptothecin to a human having pancreatic cancer.

DESCRIPTION OF THE PREFERRED EMBODIMENT(S)

While treatment of mammals with 20(S)-camptothecin compounds showed promise for treating various forms of cancer, upon using camptothecin compounds with humans, it was found that the success rate was less than expected in view of the results achieved with mice. Thus far, a success rate of partial and/or complete remissions of various cancer tumors in humans was achieved with various 20(S)-camptothecin compounds. It was quite unexpected that by treating pancreatic cancer in humans with 20(S)-camptothecin compounds and preferably 9-Nitro-20(S)-camptothecin or 9-Amino-20(S)-camptothecin, that a partial and/or complete remission occurred in at least about 35% of the human patients treated.

CPT is a plant alkaloid isolated from *Camptotheca acuminata*. Chemical derivatives of CPT can be prepared either in a semisynthetic or totally synthetic way. (See, e.g., Wani, M. C. et al., *J. Med. Chem.* 23:544, 1980; Wani, M. C. et al., *J. Med. Chem.* 30: 1774 (1987); and Wani, M. C. et al., *J. Med. Chem.* 30: 2317 (1987)).

In the example discussed below, the CPT was obtained from the Institute of Materia Medica, Academia Sinica, Shanghai, China, and further purified using standard chromatographic techniques. Camptothecin Sodium Salt (CPT Na+), 9-Nitro-20(S)-Camptothecin (9NO$_2$) and 9-Amino-20 (S)-Camptothecin (9AC) were also synthesized from CPT. CPT and derivatives thereof have to be extensively purified prior to administering for use in the present invention because: (1) the natural product contains several other components which have a large degree of toxicity for example, in mice, and (2) FDA regulations require such purifying for any drug or compound to be used as a medicine. Methods of purification known by those skilled in the art can be used, e.g.—dissolving the CPT in a suitable solvent such as chloroform or methylene chloride and then adsorbing onto a column containing silica gel and then carrying out elution of the adsorbed materials by increasing the polarity of the eluant by adding, e.g., methanol.

The purity of the compound can be tested by high performance liquid chromatography (HPLC) and thin layer chromatography (TLC) and other appropriate methods known in the art. The compound can also be completely characterized using infrared (IR), ultraviolet (UV) and nuclear magnetic resonance (NMR) spectroscopy and elemental analysis.

Furthermore, the CPT and derivatives thereof used in the present invention are water-insoluble and not administered in the chemically and physically different sodium salt form. This difference can easily be observed by looking at their elemental analysis, NMR, UV and IR spectra and also by their different physical behavior in HPLC and TLC experiments.

CPT and derivatives thereof of the closed lactone ring form are used and are administered in any form, preferably intramuscularly, orally, or transdermally and in some cases it was possible to obtain total remission of human pancreatic cancer. The derivatives of CPT for use in the present invention include, for example, 9NO$_2$, and 9AC. A mixture of CPT and derivatives thereof can also be used in the present invention.

Other related derivatives can also be used in conjunction with the method of the present invention. Examples include dimethylaminomethyl-10-hydroxy-20(S)-CPT (topotecan), 7-ethyl-10-[4-(1-piperdino)-1-piperdino]carbonyloxy-CPT (CPT-11), 7-ethyl-10-hydroxy-20(S)-CPT, 9-amino-20(S)-CPT, 9-nitro-20(S)-CPT, 10,11-methylenedioxy-20(S)-CPT, 9-chloro-20(S)-CPT, 9-bromo-20(S)-CPT, 9-hydroxy-20 (S)-CPT, 11-hydroxy-20(S)-CPT, and 10-hydroxy-20(S)-CPT.

Another method of administering the compounds of the present invention is by a transdermal or transcutaneous route. One example of such an embodiment is the use of a patch. In particular, a patch can be prepared with a fine suspension of a compound disclosed in the present application in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well. The patch can contain the CPT compound in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

In the studies, the water-soluble derivatives of these compounds proved to be ineffective as anticancer agents and very toxic to mammals. Even the closed lactone ring forms of CPT and derivatives thereof showed a great difference in activity, depending on their route of administration.

As used herein, the term "pancreatic cancer" is intended to encompass all forms of human pancreatic carcinomas, sarcomas, and melanomas which occur in the poorly differentiated, moderately differentiated, and well differentiated forms.

In treating or retarding malignant tumors in mammals in accordance with the present invention, the aforedescribed camptothecin compounds are administered in any form, preferably intramuscularly, transdermally, or orally, using commonly known methods, for example, gelatin capsules for oral administration, as well as novel, superior formulations, such as microsuspensions in lipid and in lipid-like emulsions (e.g.—Intralipid 20, cottonseed oil and peanut oil) for intramuscular administration and inclusion in cholesterol pellets for subcutaneous long-term administration.

As used herein, an "effective amount" of CPT and derivatives thereof described above is intended to mean that amount of the compound which will inhibit the growth of, or retard pancreatic cancer, or kill malignant pancreatic cells, and cause the regression and palliation of malignant pancreatic tumors, i.e., reduce the volume or size of such tumors or eliminate the tumor entirely.

With humans, the effective amounts can be administered on the basis of body surface area. The interrelationship of dosages for animals of various sizes, species and humans (based on mg/M$^2$ of body surface) is described by E. J. Freireich et al., *Cancer Chemother. Rep.*, 50(4):219 (1966). Body surface area may be approximately determined from the height and weight of an individual (see, e.g., *Scientific Tables*, Geigy Pharmaceuticals, Ardsley, N.Y. pp. 537–538 (1970). An effective amount of the camptothecin compounds in the present invention can range from about 0.5 mg/m$^2$ of body surface per day to about 2.0 mg/m$^2$ of body surface per day, preferably about 1.0 mg/m$^2$ of body surface per day to about 1.5 mg/m$^2$ of body surface per day. Preferably, this dosage is administered each day for five days and then two days with no dosage, and so on. The exact timing of administration of the dosages can be varied to achieve optimal results.

Another important feature of the method provided by the present invention relates to the relatively low or no apparent overall toxicity of the camptothecin compounds administered in accordance herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity.

The compounds of the present invention may be administered in combination with pharmaceutically acceptable carriers or diluents, such as Intralipid 10 or 20 or natural oils, or other suitable emulsifiers for lipophilic compounds.

The present invention will be further clarified by the following example, which is intended to be purely exemplary of the present invention.

EXAMPLE 1

Ten human patients diagnosed with pancreatic cancer were administered 9-nitro-20(S)-camptothecin. 9NO$_2$ (also referred to as 9NC) was synthesized (Wani, M. C., Nicholas, A. W., Wall, M. E., Plant Tumor Agents. 23. Synthesis and antileukemic Activity of Camptothecin analogues, *J. Med. Chem.*, 2358–2363, 1986) from CPT obtained from the Institute of Materia Medica, Academia Sinica, Shanghai, China. The derivatives were purified by chromatography and analyzed. A typical sample preparation for oral administration includes the dispersion of the test compound by sonication (3 pulses for 30 seconds each), using an Ultrasonic Processor, Model GE600 by Sonics and Materials, Inc., CT.

The dosage of the 9-nitro-20(S)-camptothecin is set forth in Table 1, as well as the sex, age, and starting date of the treatment. To date, there have been two cases of complete remission, and other patients show signs of at least partial remissions. One patient has died, but it is noted that this patient did survive over a year and treatment with the 9-nitro-20(S)-camptothecin at least contributed to that survival of over a year. This is important because, without treatment, a patient has a life expectancy of about 4.6 months upon detection of the pancreatic tumor and with other known treatments has a life expectancy of about 5.5 to about 6.5 months. Thus, even though one patient has died, the patient's survival for over one year was still unexpected and superior to other forms of treatment.

The patients set forth in Table 1 were administered the various dosages orally wherein crystalline 9-nitro-20(S)-camptothecin powder was administered in the form of gelatin capsules as described earlier.

TABLE 1

Pancreatic Patients on 9NC

| Sex | Age | Start | Off | Total Dose | Remarks |
|---|---|---|---|---|---|
| Male | 59 | 8/1/96 | | 2.5 mg/day | Subjective improvement; has liver mets; large central mass--has gone back to work. |
| Male | 54 | 3/16/95 | 4.96 | 3.0 mg/day (decreased to 2.0 mg/day 8/95) | Complete remission, tumor-free over one year. |
| Male | 42 | 6/23/95 | 2/20/96 | 4 mg/day | Died; Progression on CAT scan eventually, but did survive over a year. |
| Male | 50 | 11/3/95 | Present | 2.25 mg/day | Complete remission, tumor-free over six months. |
| Male | 54 | 5/22/96 | Present | 3.0 mg/day, increased to 3.25 mg/day 7/96 | Liver and peritoneal mets and ascites; CEA antigen dropped from 100 to 19; ascites gone. |
| Male | | 7/8/96 | | 2.25 mg/day | |
| Female | 56 | 7/3/96 | | 3.00 mg/day | Developed low WBC; interrupted and restarted. |
| Male | 67 | 7/31/96 | | 2.00 mg/day | |
| Male | 51 | 8/26/96 | | 3.5 mg/day | Has gained five pounds and feels well. |
| Female | 52 | 8/7/96 | | 1 mg/day | |

As also described earlier, it is unexpected and superior to have out of ten patients, two complete remissions, overall favorable initial results regarding the other patients, and one patient who survived over a year before dying. With human patients having other forms of cancer being treated with 20(S)-camptothecin compounds, there has been an approximately 15% partial and/or complete remission. For humans, the present invention is quite unexpected and superior in its treatment of pancreatic cancer.

As reflected in the Figure, the patient who was started on May 22, 1996 initially had a CA 19-9 antigen count well above 40,000 and a carcino-embryonic antigen (CEA) level well above 100. After about 60 days of treatment with 9-nitro-20(S)-camptothecin, these levels dropped below 10,000 for the CA 19-9 antigen count and below 20 for the CEA count. Clearly, the unexpected and quite effective results of treating patients with camptothecin compounds can be seen with these results since these two antigen counts are directly related to the presence of pancreatic cancer in humans.

It is clear from these studies, that CPT and its derivatives with the closed lactone ring have been demonstrated to possess an astonishing level of anticancer activity with respect to pancreatic cancer in humans. The method of the present invention has been able to block growth completely and to totally regress human pancreatic cancer. This has been accomplished without any observable toxicity.

Other embodiments of the present invention will be apparent to those skilled in the art from consideration of the specification and practice of the present invention disclosed herein. It is intended that the specification and examples be considered as exemplary only, with a true scope and spirit of the invention being indicated by the following claims.

What is claimed is:

1. A method of treating pancreatic cancer in a human comprising administering to said human an effective amount of a water-insoluble 20(S)-camptothecin compound with a closed-lactone ring, a derivative thereof or mixture thereof, wherein said 20(S)-camptothecin compound is 20(S)-camptothecin, 9-Nitro-20(S)-camptothecin, 9-Amino-20(S)-camptothecin, or a mixture thereof, and wherein said effective amount is at least about 1 mg/day.

2. The method of claim 1, wherein said 20(S)-camptothecin compound is 9-Nitro-20(S)-camptothecin.

3. The method of claim 1, wherein said 20(S)-camptothecin compound is administered orally.

4. The method of claim 1, wherein said 20(S)-camptothecin compound is administered or intramuscularly.

5. The method of claim 1, wherein said 20(S)-camptothecin compound is administered transdermally.

6. The method of claim 1, wherein said 20(S)-camptothecin compound is 9-amino-20(S)-camptothecin.

7. The method of claim 1, wherein said 20(S)-camnptothecin compound is 20(S)-camptothecin.

8. The method of claim 1, wherein said effective amount is from about 1 mg/day to about 4 mg/day.

9. The method of claim 1, wherein said effective amount is from 1 mg/day to 4 mg/day.

* * * * *

UNITED STATES PATENT AND TRADEMARK OFFICE
CERTIFICATE OF CORRECTION

PATENT NO. : 6,080,751
DATED : June 27, 2000
INVENTOR(S) : John S. Stehlin, Ethan A. Natelson, Beppino C. Giovanella, And Anthony J. Kozielski It is certified that error appears in the above-identified patent and that said Letters Patent is hereby corrected as shown below:

Title page, item [63]
Line 3, after abandoned, insert -- which is a continuation of application No. 08/301,727, filed September 7, 1994, pat.No. 5,552,154, --;
Line 5, delete "and a continuation-in-part of application No. 07/432,066, Nov. 6, 1989, Pat. No. 5,225,404".

Column 1,
Line 8, after "5,652,244," insert -- which is a continuation of U.S. Application No. 08/301,727, filed September 7, 1994, now U.S. Patent No. 5,552,154, --;
Lines 12 and 13, delete "and also a continuation-in-part of U.S. Ser. No. 07/432,066, filed Nov. 6, 1989, now U.S. Patent No. 5,225,404".

Signed and Sealed this

Thirty-first Day of July, 2001

*Attest:*

Nicholas P. Godici

*Attesting Officer*

NICHOLAS P. GODICI
*Acting Director of the United States Patent and Trademark Office*